(12) United States Patent
Smith et al.

(10) Patent No.: US 9,693,686 B2
(45) Date of Patent: Jul. 4, 2017

(54) OPHTHALMIC VISUALIZATION DEVICES, SYSTEMS, AND METHODS

(71) Applicant: NOVARTIS AG, Basel (CH)

(72) Inventors: Ronald T. Smith, Irvine, CA (US); Lingfeng Yu, Rancho Santa Margarita, CA (US); Michael Papac, North Tustin, CA (US); Argelio Michael Olivera, Mission Viejo, CA (US); Steven T. Charles, Memphis, TN (US)

(73) Assignee: NOVARTIS AG (CH)

( * ) Notice: Subject to any disclaimer, the term of this patent is extended or adjusted under 35 U.S.C. 154(b) by 0 days.

(21) Appl. No.: 15/043,064

(22) Filed: Feb. 12, 2016

(65) Prior Publication Data

US 2016/0317032 A1    Nov. 3, 2016

Related U.S. Application Data

(60) Provisional application No. 62/155,181, filed on Apr. 30, 2015.

(51) Int. Cl.
*A61B 3/14* (2006.01)
*A61B 3/10* (2006.01)
(Continued)

(52) U.S. Cl.
CPC .............. *A61B 3/13* (2013.01); *A61B 3/0025* (2013.01); *A61B 3/1015* (2013.01); *A61B 3/12* (2013.01);
(Continued)

(58) Field of Classification Search
USPC .................................................. 351/200–246
See application file for complete search history.

(56) References Cited

U.S. PATENT DOCUMENTS 7,338,170 B2    3/2008  Cech et al.
7,499,219 B2    3/2009  Cech et al.
(Continued)

FOREIGN PATENT DOCUMENTS

EP    1308124 A2    5/2003
EP    1321095 A2    6/2003
(Continued)

OTHER PUBLICATIONS

Written Opinion of the International Searching Authority, International Application No. PCT/IB2016/052420, dated Jul. 15, 2016, 7 pages.
(Continued)

*Primary Examiner* — Mohammed Hasan (57) ABSTRACT

Systems, apparatuses, and methods of and for an ophthalmic visualization system are disclosed. An example ophthalmic visualization system may include a first lens positioned relative to a surgical microscope in a manner facilitating viewing of a central region of a retina through the surgical microscope during a surgical procedure. The first lens may be positionable in an optical path between an eye and the surgical microscope during the surgical procedure. The example ophthalmic visualization system may also include a second lens selectively positionable relative to the surgical microscope and the first lens in a manner facilitating viewing of a peripheral region of the retina of the eye during the surgical procedure. The second lens may be selectively positionable in the optical path such that the peripheral region is selectively viewable without changing the position of the first lens during the surgical procedure.

20 Claims, 9 Drawing Sheets

(51) Int. Cl.
*A61B 3/13* (2006.01)
*A61B 3/12* (2006.01)
*A61B 3/00* (2006.01)
*A61B 3/125* (2006.01)
*G02B 27/00* (2006.01)

(52) U.S. Cl.
CPC .......... *A61B 3/125* (2013.01); *G02B 27/0068* (2013.01)

(56) References Cited

U.S. PATENT DOCUMENTS

| | | | |
|---|---|---|---|
| 7,946,706 B2 | 5/2011 | Cech et al. | |
| 8,556,885 B2* | 10/2013 | Hohla | A61B 5/117 606/10 |
| 2008/0117432 A1* | 5/2008 | Reimer | A61B 3/102 356/511 |
| 2008/0297892 A1* | 12/2008 | Abele | A61B 3/13 359/389 |
| 2014/0063463 A1 | 3/2014 | Zhou et al. | |

FOREIGN PATENT DOCUMENTS

| | | |
|---|---|---|
| WO | 2011053512 A1 | 5/2011 |
| WO | 2016174613 A1 | 11/2016 |

OTHER PUBLICATIONS

Ohiji, M., Tada, E, & Futamura, H. Combining a Contact Lens and Wide-Angle Viewing System for a Wider Fundus View. Retina, The Journal of Retinal and Vitreous Diseases, (2011) 31(9), 1958-1960.
2006 Volk Optical Inc. Catalog.
Ma, et al. (2014) Content-Adaptive High-resolution Hyperspectral Video Acquisition with a Hybrid Camera System.
Quilliet, et al. Electrowetting: a recent outbreak, Current Opinion in Colloid & Interface Science (2001), 6, 34-39.
Holoeye Spatial_Light_Modulators (LC2012) (Oct. 26, 2015).
Roorda, A., Adaptive optics for studying visual function: A comprehensive review. Journal of Vision, (2011), 11(5):6, 1-21.
Ocular Instruments—Landers 50 deg (wayback machine Sep. 20, 2012) (Oct. 25, 2015).
Ocular Instruments—Peyman Wessels Landers 132D (wayback machine Jul. 21, 2012) (Oct. 25, 2015).
Ocular Instruments—Tolentino 30 deg prism (wayback machine Jan. 22, 2014) (Oct. 25, 2015).
Ocular Instruments—Woldof prismatic biconcave vit lens (wayback machine Jan. 22, 2014) (Oct. 25, 2015).
Ocular Instruments Lens Ring System (2001).
Simon, et al., Optical design rules of a camera module with a liquid lens and principle of command for AF and OIS functions.(2010).
Simon, et al., Optical image stabilization with a liquid lens. (2010).
D3128 Spatial Light Modulator User's Manual (Rev 1.04).
Maillard, et al. Two Liquids Wetting and Low Hysteresis Electrowetting on Dielectric Applications. Langmuir, (2009), 25 (11), 6162-6167.
Berge, et al., Variable focal lens controlled by an external voltage: An application of electrowetting. Eur. Phys. J.E. 3, 159-163 (2000).
Varioptic electrowetting (wayback machine Feb. 21, 2013) (Oct. 26, 2015).
Varioptic Liquid Lens Technology (2010).
Volk Flat and 45 Prism SSV ACS (from Mar. 11, 2014).
Shamai, R., et al., Water, electricity, and between . . . On electrowetting and its applications. Soft Matter, 2008, 4, 38-45.
PCT/IB2016/052420, International Search Report, International Searching Authority, Jul. 15, 2016, 4 pgs.
Ohno, "Combined use of high-reflective index vitrectomy meniscus contact lens and a noncontact wide-angle viewing system in vitreous surgery"; Clinical Ophthalmology; 2011:(5) 1109-1111.

* cited by examiner

OPHTHALMIC VISUALIZATION DEVICES, SYSTEMS, AND METHODS

CROSS REFERENCE TO RELATED APPLICATIONS

This application claims the benefit of U.S. Provisional Application No. 62/155,181, filed Apr. 30, 2015, the contents of which are incorporated herein by reference.

TECHNICAL FIELD

The present disclosure is directed to ophthalmic visualization devices, systems, and methods. More particularly, but not by way of limitation, the present disclosure is directed to devices, systems, and methods of selectively and efficiently visualizing central and peripheral regions of the fundus/retina of an eye.

BACKGROUND

Figure 1:
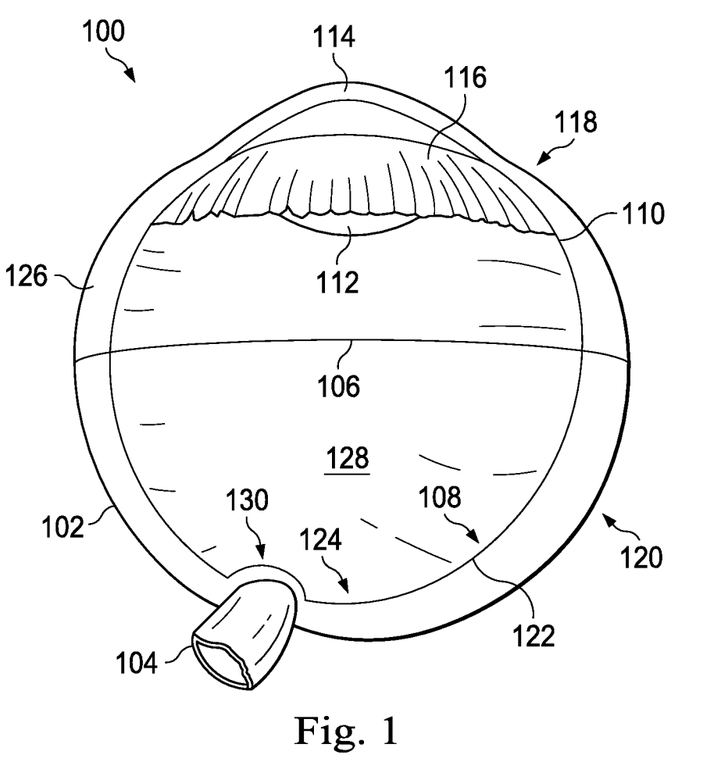
FIG. 1 is an illustration of an eye.

During certain ophthalmic surgical procedures, a user, such as a surgeon or other medical professional, may need to visualize various parts of a patient's eye. An example eye 100 is illustrated in FIG. 1. The eye 100 includes a globe 102 connected to an optic nerve 104, with the globe divided into an anterior segment 118 and a posterior segment 120. The anterior segment 118 includes a lens 112, a cornea 114, and an iris 116. The posterior segment 120 includes a fundus 108 that defines an interior surface of the eye 100. The fundus 108 includes a retina 122, a macula 124, and an optic disk 130. The posterior segment 120 is filled with vitreous humor 128. The optic nerve 104 extends from the posterior segment 120 of the eye 100. To access the interior of the eye 100, a user may penetrate the globe 102 via an incision in a sclera 126. During a vitreoretinal surgical procedure, for example, the user typically views a central portion of the fundus 108, including the area around a macula 124 and/or an optic disk 130. The user, however, may also be required to view a periphery of the fundus 108, including the area around an equator 106 of the globe 102 and to an ora serrata 110, which defines a border between the retina 122 and more anterior portions of the eye 100.

During a surgical procedure, a user may employ one of three different types of lenses, in combination with a surgical microscope, to view the fundus 108. These include a direct contact lens, an indirect contact lens, and an indirect non-contact lens. A direct contact lens allows a user to view a central portion of the fundus 108. However, viewing the periphery of the fundus 108 is not possible with a direct contact lens because it provides only a narrow field of view. An indirect contact lens provides a wider field of view than a direct contact lens. However, indirect contact lenses may be top-heavy and typically move in angular and positional orientation after initial placement on the eye. Accordingly, a user usually requires the help of an assistant, either to continually hold the indirect contact lens in place or to frequently reposition the lens many times during the course of the surgical procedure. These inefficiencies make the indirect contact lens an unpopular choice among some users. Further, because there is an inverse relationship between retinal resolution and retinal field of view, the resolution of the observed fundus decreases as the field of view increases. Relatively lower resolution may make the surgical procedure more challenging for the user.

Some of the positional instabilities associated with the indirect contact lens may be addressed by an indirect non-contact lens, which is attached to the surgical microscope instead of being contacted directly to the eye. However, the indirect non-contact lens may not provide as wide of a field of view of the fundus as the indirect contact lens. In order to see beyond the region of fundus viewable with the indirect non-contact lenses, the surgeon may indent a peripheral region of the sclera to push the fundus in that region into the lens's field of view or may rotate the eye off-axis, or both. Rotating the eye may include moving the patient's head into an uncomfortable manner. Having to frequently rotate the eyeball and/or depress the sclera to view peripheral regions of the fundus is undesirable because it may cause more trauma for the patient, may constitute extra steps for the user to perform, may increase the surgery time, and may increase the likelihood of surgical complications.

SUMMARY

According to one aspect, the present disclosure is directed to an ophthalmic visualization system including a first lens positioned relative to a surgical microscope in a manner facilitating viewing of a central region of a retina through the surgical microscope during a surgical procedure. The first lens may be positionable in an optical path between an eye and the surgical microscope during the surgical procedure. The ophthalmic visualization system may also include a second lens selectively positionable relative to the surgical microscope and the first lens in a manner facilitating viewing of a peripheral region of the retina of the eye during the surgical procedure. The second lens may be selectively positionable in the optical path such that the peripheral region is selectively viewable without changing the position of the first lens during the surgical procedure.

Another aspect of the present disclosure is directed to an ophthalmic visualization system including a direct contact lens positionable on an eye of a patient and in an optical path of a surgical microscope, a prismatic off-axis lens selectively positionable in the optical path between the direct contact lens and the surgical microscope, and an indirect non-contact lens positioned in the optical path between the direct contact lens and the surgical microscope. A peripheral region of a retina of the eye may be viewable without moving the eye when the prismatic off-axis lens is positioned in the optical path. A central region of the retina may be viewable without moving the eye when the prismatic off-axis lens is removed from the optical path.

A third aspect of the disclosure is directed to a method of visualizing an eye undergoing an ophthalmic surgical procedure. The method may include positioning an indirect non-contact lens in an optical path between an eye and a surgical microscope to view a central region of a retina of the eye. The method may also include selectively positioning a prismatic off-axis lens in the optical path between the eye and the indirect non-contact lens to view a peripheral region of the retina without moving the eye and without moving the indirect non-contact lens.

The various aspects of the disclosure may include one or more of the following features. The first lens may be an indirect non-contact lens. The second lens may be a prismatic off-axis lens. The second lens may be aligned with and rotatable about an alignment axis of the surgical microscope such that different portions of the peripheral region are selectively viewable. The first lens may be coupled to the surgical microscope. The second lens may be moveably coupled to the first lens. A third lens may be positioned and arranged to correct aberrations of light reflected from the fundus and transmitted through the eye. The third lens may be positioned in the optical path adjacent to the eye. The third lens may be a direct contact lens. A wavefront correction apparatus may be disposed between the microscope and the first lens. The wavefront correction apparatus may be arranged to remove optical aberrations from an image viewable through the microscope. The wavefront correction apparatus may include a beam splitter in the optical path and a wavefront corrector. The beam splitter may be configured to direct a first portion of light from the optical path for processing. The wavefront corrector may be configured to modify a phase of a second portion of light based on the processed first portion. A proximity sensor may be coupled to at least one of the first lens and the second lens. The proximity sensor may be configured to monitor a distance between said at least one of the first lens and the second lens and the eye. An image shifting apparatus may be structurally configured to move an image of the retina into alignment with an alignment axis of the surgical microscope for viewing.

The various aspects of the disclosure may also include one or more of the following features. A direct contact lens may be positioned on a cornea of the eye. The prismatic off-axis lens may be rotated to view different portions of the peripheral region of the retina.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate implementations of the systems, devices, and methods disclosed herein and together with the description, serve to explain the principles of the present disclosure.

These figures will be better understood by reference to the following Detailed Description.

DETAILED DESCRIPTION

For the purposes of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one or more implementations may be combined with the features, components, and/or steps described with respect to other implementations of the present disclosure. For simplicity, in some instances the same reference numbers are used throughout the drawings to refer to the same or like parts.

The present disclosure relates generally to devices, systems, and methods for visualizing the central and peripheral regions of the fundus. Ophthalmic visualization systems of the present disclosure include a prismatic off-axis lens and an indirect non-contact lens that are positioned in an optical path between the surgical site, such as an eye, and the surgical microscope. The prismatic off-axis lens may be selectively positioned in or removed from the optical path. When the prismatic off-axis lens is positioned in the optical path, the user may view the periphery of the fundus. When the prismatic off-axis lens is removed, the user may view the central portion of the fundus. The ophthalmic visualization system may also include a direct contact lens that minimizes optical aberrations associated with the patient's cornea. These aberrations could otherwise potentially degrade the image viewed by the user.

The devices, systems, and methods of the present disclosure provide numerous advantages. For example, the devices, systems, and methods allow viewing of peripheral regions of the retina and/or fundus without rotating the eye and/or indenting the sclera. The devices, systems, and methods of the present disclosure also allow for a wide field of view without the positional instability of an indirect contact lens. The user may selectively and efficiently switch between viewing peripheral and central regions of the fundus simply by sliding a prismatic off-axis lens into and out of an optical path of the surgical microscope. The user may also selectively and efficiently view different portions of the periphery by simply rotating the prismatic off-axis lens.

Devices, systems, and methods of the present disclosure also provide increased convenience to a surgeon during a surgical procedure by utilizing self-retaining optical elements, minimizing the need for an assistant to reposition optical elements, and providing easy lens switching. According to the present disclosure, a relatively high resolution retina image may be generated because optical aberrations may be compensated by a direct contact lens and/or a wavefront correction apparatus. Additionally, the present disclosure may minimize or correct for aberrations caused by corneal dryness, correct image blur associated with refractive index-matched gels and/or liquids positioned between the eye and a direct contact lens, remove marks on the cornea as a result of contact with the lens, and minimize condensation and/or droplets on and/or within the lens.

Figure 2:
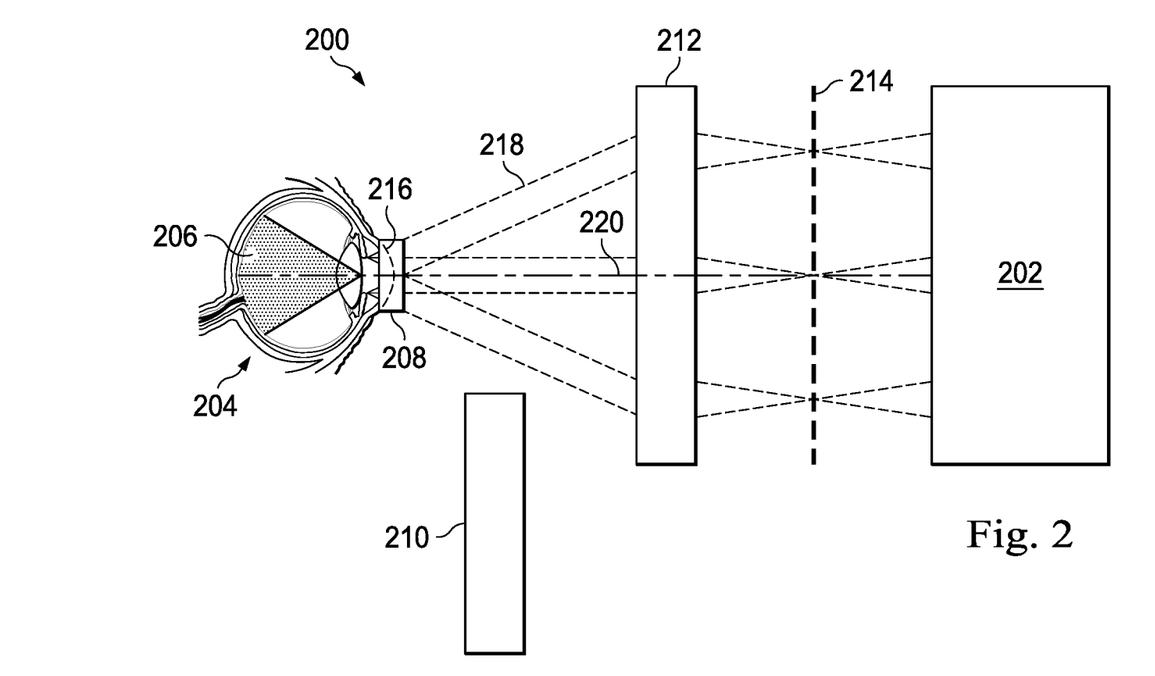
FIG. 2 is an illustration of an example ophthalmic visualization system including a direct contact lens, an indirect non-contact lens and a prismatic off-axis lens removed from an optical path.

FIG. 2 illustrates an example ophthalmic visualization system 200. The system 200 includes a surgical microscope 202, an indirect non-contact lens 212, a prismatic off-axis lens 210, and a direct contact lens 208. The system 200 may be used in various ophthalmic procedures, such as a posterior segment procedure, a vitreoretinal procedure, a vitrectomy procedure, a pars plana vitrectomy, and/or other desired procedures. A user, such as a surgeon or other health care provider, views an interior of an eye 204 using the surgical microscope 202. That is, the surgical microscope 202 receives light 218 reflected from the eye 204. The surgical microscope 202 may be any microscope suitable for use in an ophthalmic procedure. The surgical microscope 202 may include one or more lenses, such as one or more focusing lenses, one or more zoom lenses, and an objective lens. The surgical microscope 202 may also include one or more mirrors, filters, gratings, and/or other optical components. These components, or a group thereof, may form all or a part of an optical train of the surgical microscope 202.

The indirect non-contact lens 212 may be positioned in the optical path between the surgical microscope 202 and the eye 204. The indirect non-contact lens 212 may include one or more optical components. For example, in some instances, the indirect non-contact lens 212 may include one or more of a biconcave lens, biconvex lens, convex-concave lens, plano concave lens, plano convex lens, positive/negative meniscus lens, aspheric lens, converging lens, diverging lens, prism lens, other suitable lenses, mirrors, and/or combinations thereof. The indirect non-contact lens 212 may be a single optical component or an assembly of more than one optical component. The indirect non-contact lens 212 interacts with light 218 reflected from the eye 204 to create an inverted real image, referred to as an intermediate image, in front of the lens 212 (e.g., between the lens 212 and the surgical microscope 202). The user focuses the surgical microscope 202 on an intermediate image plane 214 to view the inverted image. In this manner, the user may indirectly view the fundus. In some implementations, the surgical microscope 202 may include an inverter lens to re-invert the image so that the user views an upright image. In other implementations, the inverter lens may be positioned in the optical path between the surgical microscope 202 and the eye 204, such as between the surgical microscope 202 and the indirect non-contact lens 212. The intermediate image in FIG. 2 is aligned with an alignment axis 220 of the surgical microscope 202. Thus, the user views the intermediate image in the center of the optical path using the surgical microscope 202.

The direct contact lens 208 may be positioned in the optical path between the surgical microscope 202 and the eye 204. The direct contact lens 208 may be adjacent the eye 204. For example, the direct contact lens 208 may be in physical contact with the cornea 216. The direct contact lens 208 may have a concave surface on a side that contacts the cornea 216. This may allow the direct contact lens 208 to comfortably receive the convex surface of the cornea 216 without indenting the cornea 216. The direct contact lens 208 may include or be formed of one or more optical components, such as a biconcave lens, biconvex lens, convex-concave lens, plano concave lens, plano convex lens, positive/negative meniscus lens, aspheric lens, converging lens, diverging lens, prism lens, other suitable lenses, mirrors, and/or combinations thereof. The direct contact lens 208 may be a single optical component or an assembly of more than one optical component. In some implementations, the direct contact lens 208 is embedded in a stabilizing mechanism. The stabilizing mechanism may be configured to stabilize the direct contact lens 208 relative to the eye 204. To that end, the stabilizing mechanism may include or be formed of one or more of a trocar, a counter weight, a friction-based system, an elastic system, or other system that can stabilize the direct contact lens 208 on the cornea 216.

In some examples, the direct contact lens 208 may be configured to minimize corneal surface-induced degradation of the fundus image. This may help address the challenges that arise when a cornea, such as the cornea 216, has any of various structural irregularities. When the interior of the eye 204 is viewed while the cornea 216 exposed to air, the irregular cornea/air interface refracts light in manner that may compromise the fundus image. With the direct contact lens 208 positioned on the cornea 216, a refractive index-matching gel or fluid is placed between the cornea 216 and the direct contact lens 208, thereby removing the irregular cornea/air interface. This prevents irregular refraction and unwanted, extraneous interfacial reflections (e.g., between the convex face of the cornea 216 and the concave face of the direct contact lens 208), and improves the quality of the image generated along the intermediate image plane 214.

Still referring to FIG. 2, the prismatic off-axis lens 210 may include or be formed of one or more optical components, such as a biconcave lens, biconvex lens, convex-concave lens, plano concave lens, plano convex lens, positive/negative meniscus lens, aspheric lens, converging lens, diverging lens, prism lens, other suitable lenses, mirrors, and/or combinations thereof. The prismatic off-axis lens 210 may be a single optical component or an assembly of more than one optical component. In some implementations, the prismatic off-axis lens 210 may be a relay lens.

In the implementation of FIG. 2, the prismatic off-axis lens 210 is removed from the optical path between the surgical microscope 202 and the eye 204. With the prismatic off-axis lens 210 removed from the optical path, a field of view 206, represented by the shaded portion within the eye 204, includes the central region of the fundus. For example, the user may view the retina, macula, foveola, fovea centraalis, para fovea, perifovea, optic disc, optic cup, one of more layers of the retina, vitreous, etc. The central fundus region may be viewable without moving the eye 204 and/or the indirect non-contact lens 212.

Figure 3A:
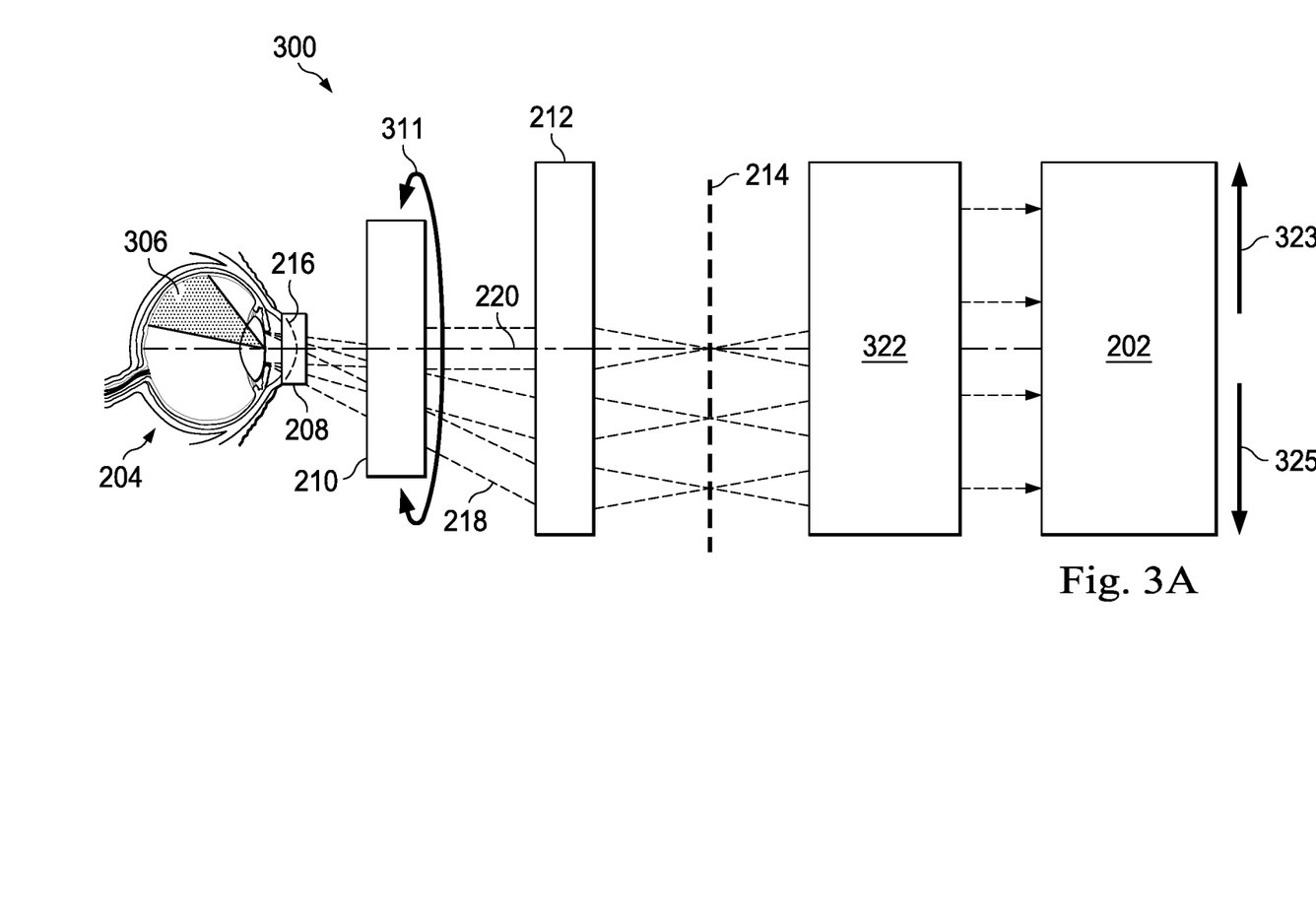
FIG. 3A is an illustration of another example ophthalmic visualization system including a direct contact lens, an indirect non-contact lens and a prismatic off-axis lens positioned in the optical path.
Figure 3B:
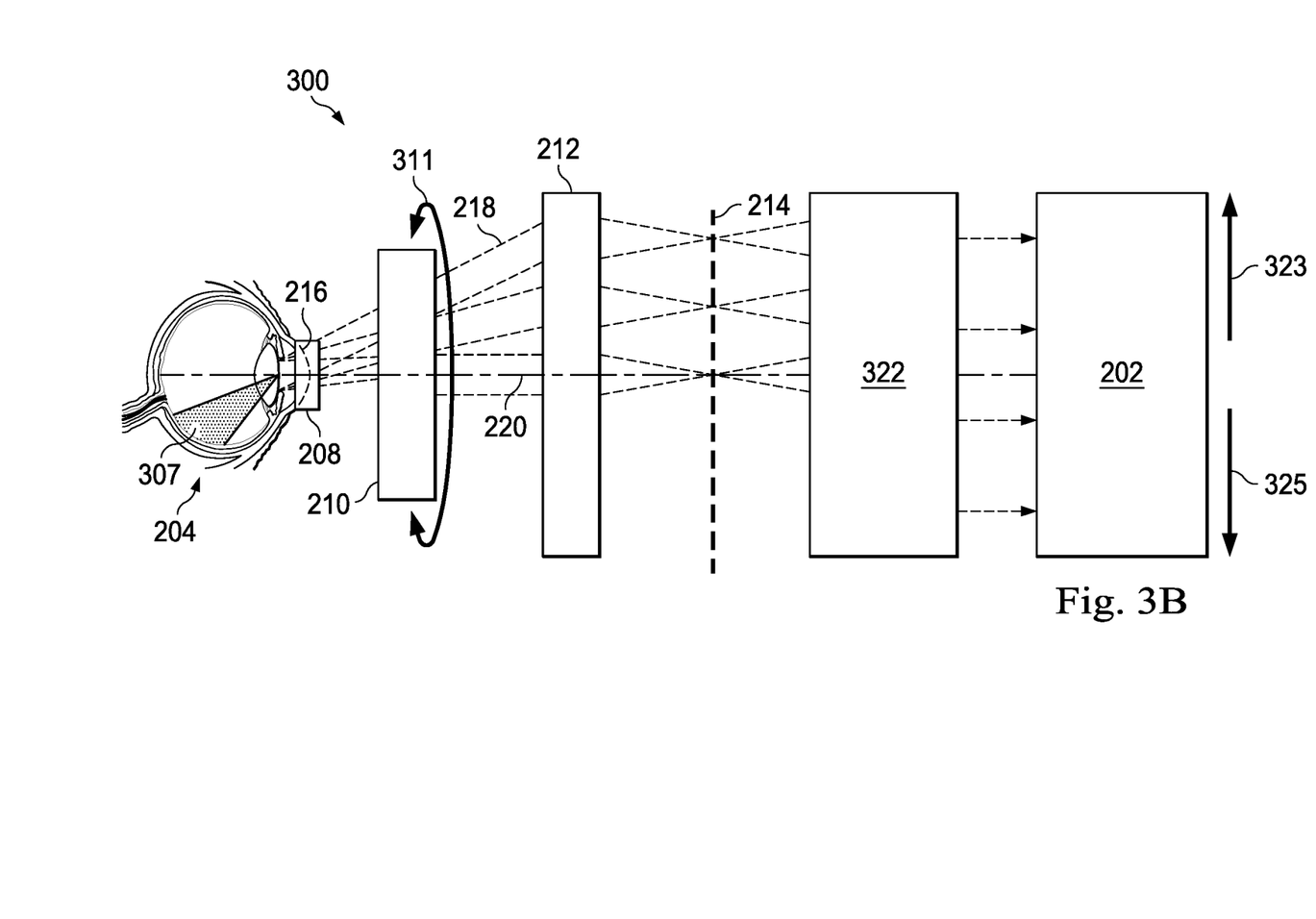
FIG. 3B is an illustration of an example ophthalmic visualization system similar to that of FIG. 3A, but with the prismatic off-axis lens rotated to view a different portion of the fundus of the eye.

FIGS. 3A and 3B illustrate an example ophthalmic visualization system 300 with the prismatic off-axis lens 210 positioned in the optical path between the surgical microscope 202 and the eye 204. FIGS. 3A and 3B include various components that are similar to those described with reference to other Figures in this disclosure, including FIG. 2. Description of the surgical microscope 202, the eye 204, the direct contact lens 208, the prismatic off-axis lens 210, the indirect non-contact lens 210, and the intermediate image plane 214 will not be repeated here, as these are described with reference to other Figures or implementations herein.

When the prismatic off-axis lens 210 is positioned in the optical path between the eye 204 and the surgical microscope 202, a peripheral region of the fundus becomes viewable to a user. As shown, the field of view 306, indicated by the shaded region within the eye 204, includes a peripheral region of the retina, for example. In the implementation of FIGS. 3A and 3B, the prismatic off-axis lens 210 is positioned in the optical path between the direct contact lens 208 and the indirect non-contact lens 212. In other implementations, the prismatic off-axis lens 210 may be positioned anywhere along the optical path between the eye 204 and the surgical microscope 202, including between the indirect non-contact lens 212 and the surgical microscope 202.

Figure 6:
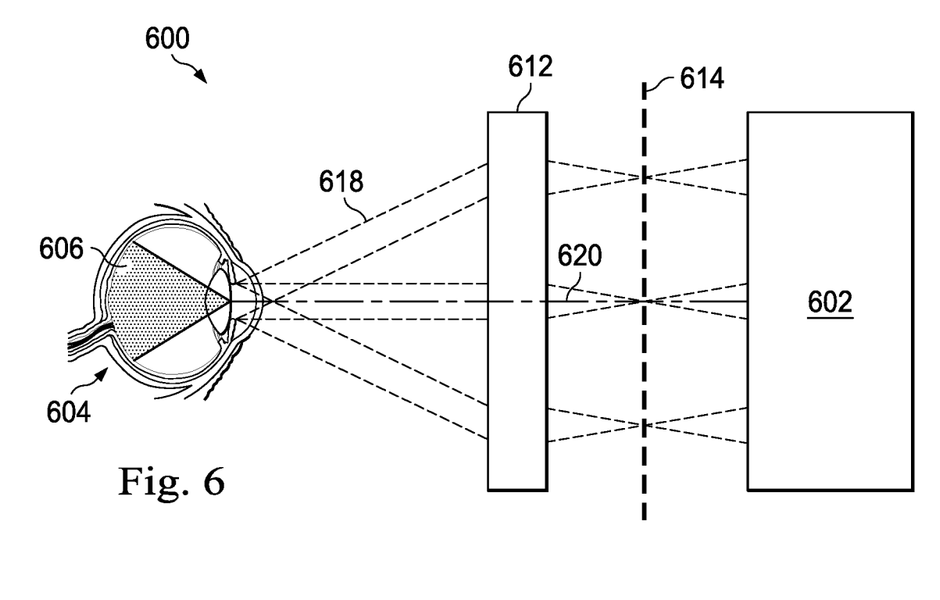
FIG. 6 is an illustration of a conventional arrangement including an indirect non-contact lens.
Figure 7:
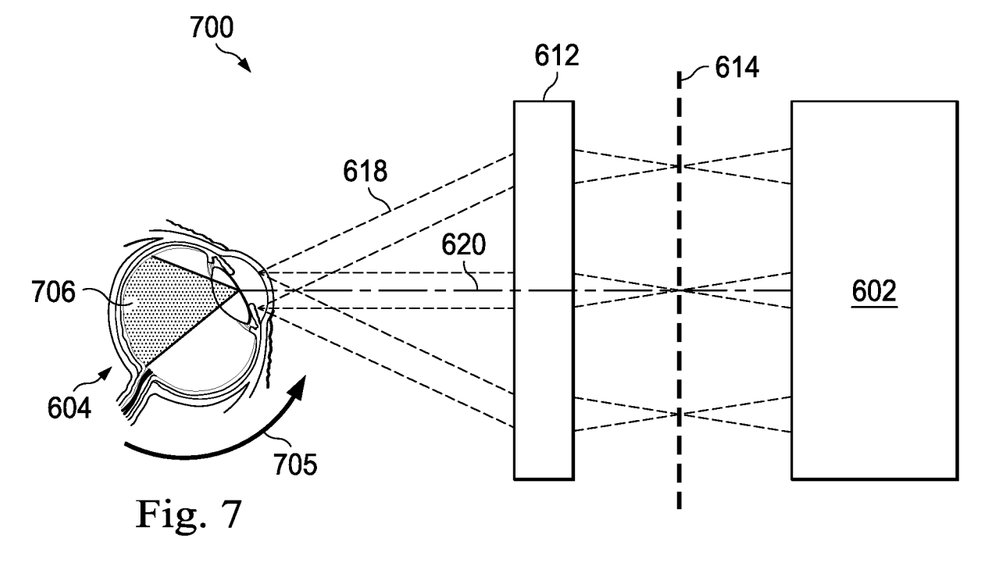
FIG. 7 is an illustration of a conventional arrangement including an indirect non-contact lens and a rotated eye.

According to exemplary aspects of the present disclosure, the user may view the peripheral region of the fundus with an indirect non-contact lens without rotating the eye and/or indenting the sclera. In contrast, viewing the periphery with an indirect non-contact lens conventionally requires such rotation and/or indentation. FIGS. 6 and 7 describe conventional arrangements 600 and 700, respectively, including only an indirect non-contact lens 612. With reference to FIG. 6, the user views an intermediate image plane 614 generated by interaction of light 618 with the indirect non-contact lens 612 using a surgical microscope 602. As shown, a field of view 606 within an eye 604 includes a central portion of the fundus, but not more peripheral portions. FIG. 7 shows an ophthalmic setup 700 in which the eye 604 is rotated relative to an alignment axis 620 of a surgical microscope 602. For example, an eye 604 may be rotated in the direction indicated by an arrow 705. Compared to the position/orientation of the eye 604 relative to the alignment axis 620 in FIG. 6, the eye 604 in FIG. 7 is offset from or misaligned from the alignment axis 620. As indicated by the shaded region within the eye that illustrates the field of view 706 in FIG. 7, more peripheral portions of the fundus are viewable when the eye 604 is rotated.

Referring again to FIGS. 3A and 3B, the prismatic off-axis lens 210 is aligned with and rotatable about the alignment axis 220 of the surgical microscope 202 such that different portions of the peripheral region are selectively viewable. For example, the prismatic off-axis lens 210 may be rotated in the direction(s) indicated by the arrow 311, about the alignment axis 220 of the surgical microscope 202. In that regard, rotation of the prismatic off-axis lens 210 may sweep out a ring- or donut-shaped viewable area of the fundus. For example, the field of view 306 of FIG. 3A, indicated by the shaded region within the eye, is viewable with the prismatic off-axis lens 210 in a particular orientation. When the prismatic off-axis lens 210 is rotated about the alignment axis 220, such as in FIG. 3B, a different portion of the peripheral region is viewable. For example, the user observes the field of view 307 when the prismatic off-axis lens 210 is rotated 180° about the alignment axis 220. Similarly, the rays depicting the light 218 in FIG. 3B are shown to be above the alignment axis 220 when the prismatic off-axis lens 210 is rotated. This is in contrast to the rays in FIG. 3A, which are below the alignment axis 220. It is understood that the directional indicators above and below are used only to for clarity in describing FIGS. 3A and 3B, and are not intending to be limiting. In various implementations, the system 300 may be oriented differently than illustrated in FIGS. 3A and 3B, and other directional indicators (e.g., left, right, etc.) may be applicable. The user may selectively rotate the prismatic off-axis lens 210 to view any desired portion of the peripheral region of the fundus. In different implementations, the prismatic off-axis lens 210 may rotatable in a clockwise and/or counterclockwise direction. The prismatic off-axis lens 210 may be rotatable between 1° and 360° about the alignment axis 220. The prismatic off-axis lens 310 may be freely rotatable in some implementations such that the rotation may exceed 360° about the alignment axis 220 in some implementations. The ophthalmic visualization system 300 also allows the user to view the peripheral region of the fundus with an indirect non-contact lens 212 without changing the position of the indirect non-contact lens 212 during the surgical procedure. For example, only the prismatic off-axis lens 210 may need to be moved into the optical path and/or rotated to view the peripheral fundus regions while the indirect non-contact lens 212 remains in the optical path.

The total field of view of the ophthalmic visualization system 300, including the central region of the fundus that is viewable with the prismatic off-axis lens 210 out of position (for example, as shown in FIG. 2) and the peripheral regions of the fundus that are viewable with the prismatic off-axis lens 310 in position (for example, as shown in FIG. 3A or FIG. 3B), is large. Any single field of view, either of the central region or the peripheral regions, may cover only a portion of the entire retinal area. Because of the inverse relationship between retinal resolution and retinal field of view, the resolution of the observed retina for the ophthalmic visualization system 300 is higher than the resolution for a system that covers a wider retinal region in one view.

The direct contact lens 208, the prismatic off-axis lens 210, and/or the indirect non-contact lens 212 may have a defined optical/optomechanical relationship with the surgical microscope 202. A defined optical/optomechanical relationship may help maintain the position and/or orientation of the direct contact lens 208, the prismatic off-axis lens 210, and/or the indirect non-contact lens 212. In some implementations, the optical/optomechanical relationship may be such that the direct contact lens 208, the prismatic off-axis lens 210, and/or the indirect non-contact lens 212 is directly or indirectly mechanically coupled to the surgical microscope 202 in a manner securing them in place relative to the surgical microscope. In some implementations, each of one of the direct contact lens 208, the prismatic off-axis lens 210, and/or the indirect non-contact lens 212 may be mechanically coupled to another of the direct contact lens 208, the prismatic off-axis lens 210, and the indirect non-contact lens 212. Direct or indirect coupling among the surgical microscope 202, the direct contact lens 208, the prismatic off-axis lens 210, and/or the indirect non-contact lens 212 may include one or more of a suspension system, a mechanical frame, a protruding arm, a conical structure, a magnetic member, an elastic member, a plastic member, and/or other coupling devices or elements. In some implementations, the direct contact lens 208, the prismatic off-axis lens 210, and/or the indirect non-contact lens 212 may be directly or indirectly coupled to another component of an ophthalmic visualization system, such as ophthalmic visualization system 200 or ophthalmic visualization system 300. In some examples, the direct contact lens 208 may be directly or indirectly mechanically coupled to a speculum.

The prismatic off-axis lens 210 and/or the indirect non-contact lens 212 are configured to selectively translate, rotate, pivot, or otherwise move into and out of the optical path between the surgical microscope 202 and the eye 204. For example, the user may translate, slide, rotate, pivot, and/or otherwise move the prismatic off-axis lens 210 into and out of the optical path to allow the user to selectively view the peripheral regions or the central region of the fundus. As another example, the prismatic off-axis lens 210 may be rotated and/or otherwise moved about the alignment axis 220 of the surgical microscope 202, in order to view any peripheral portion of the retina. The user may move the prismatic off-axis lens 210 and/or the indirect non-contact lens 212 manually, or using a motorized actuator or other mechanical and/or electromechanical controller.

Referring to FIG. 3A, the prismatic off-axis lens 210 may, depending on its orientation about the alignment axis 220, laterally shift the image generated along the intermediate image plane 214 in the direction of arrow 325. Thus, the user viewing the image through the surgical microscope 202 sees the image as laterally offset from the alignment axis 220 in the direction of the arrow 325. In some implementations, the ophthalmic visualization system 300 includes an image shifting apparatus 322 that laterally shifts the image in the direction of arrow 323 and into alignment with the alignment axis 220. Depending on the implementation, the imaging shifting apparatus 322 may include fold mirrors (e.g., two 90° fold mirrors), an optical relay system with lenses, mirrors or prisms, and/or other suitable optical elements. Similarly, in FIG. 3B, the prismatic off-axis lens 210 is rotated about the alignment axis 220 and shifts the image generated along the intermediate image plane 214 in the direction of the 323. The imaging shifting apparatus 322 laterally shifts the image in the direction of the arrow 325 and into alignment with the alignment axis 220. In the implementation of FIGS. 3A and 3B, the image shifting apparatus 322 is positioned in the optical path between the indirect non-contact lens 212 and the surgical microscope 202. In other implementations, the image shifting apparatus 322 may be positioned anywhere along the optical path between the eye 204 and the surgical microscope 202, including between the direct contact lens 208 and the prismatic off-axis lens 210, between the prismatic off-axis lens 210 and the indirect non-contact lens 212, or at other locations.

Figure 4:
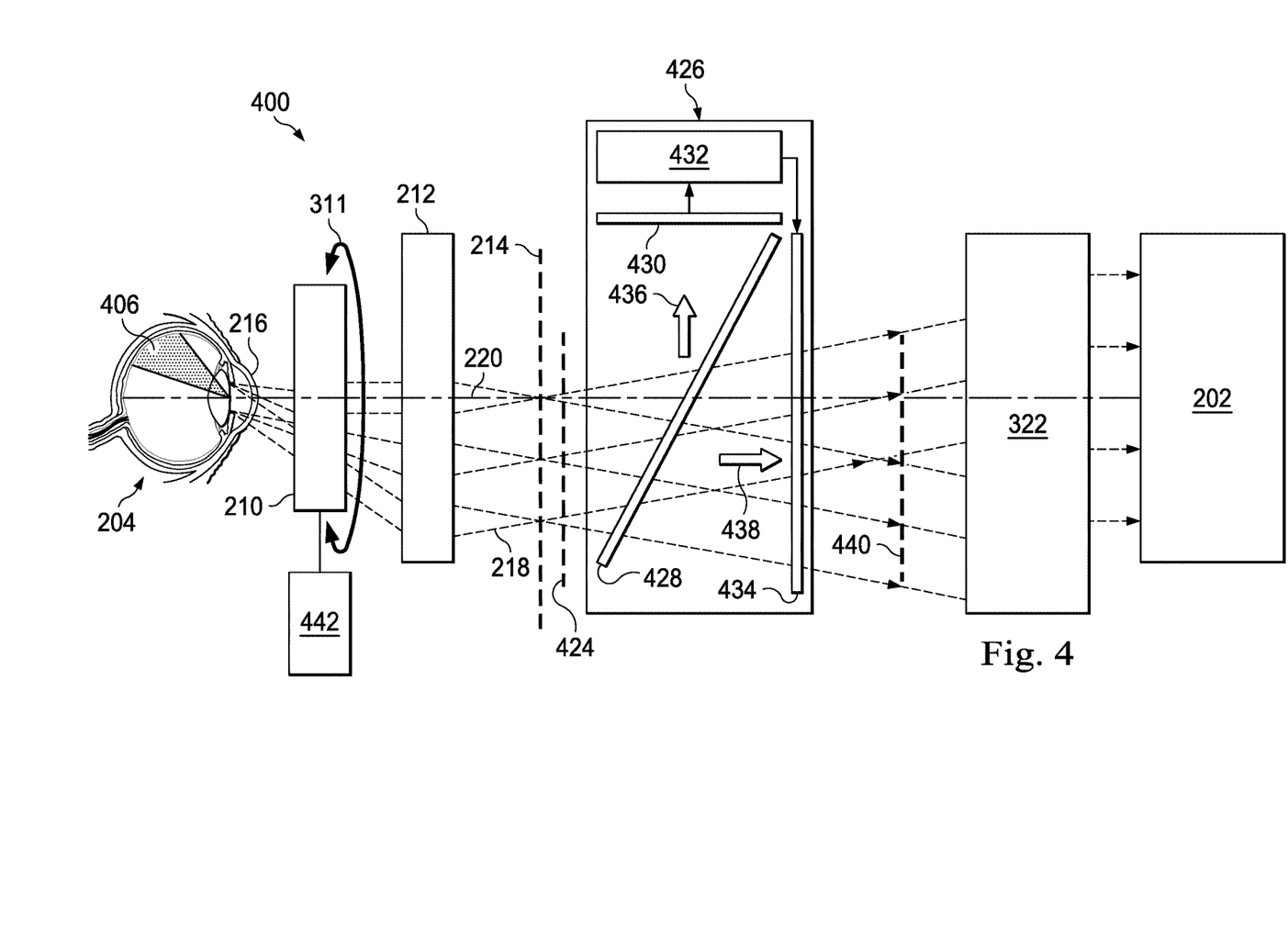
FIG. 4 is an illustration of another example ophthalmic visualization system, including an indirect non-contact lens, a prismatic off-axis lens, and a wavefront correction apparatus positioned in the optical path.

FIG. 4 illustrates an example ophthalmic visualization system 400. FIG. 4 includes various components that are similar to those described with respect to FIGS. 2 and/or 3. For ease of reading, description of the surgical microscope 202, the eye 204, the prismatic off-axis lens 210, the indirect non-contact lens 212, the intermediate image plane 214, and the imaging shifting apparatus 222 will not be repeated here, as these elements are described with reference to other Figures or implementations herein. The ophthalmic visualization system 400 does not include a direct contact lens. As described above with respect to FIG. 2, optical aberrations may result when light is refracted by an irregular surface of a cornea, such as an irregular surface of the cornea 216. The irregular surface may degrade the fundus image associated with the field of view 406 and generated along the intermediate image plane 214. Saline solution in the patient's eye, refractive errors, astigmatism, low order aberrations, and/or high order aberrations may also degrade the fundus image. In order to minimize these and other optical aberrations, the ophthalmic visualization system 400 includes a wavefront correction apparatus 426. The wavefront correction apparatus 426 receives and corrects an aberrated wavefront 424, and presents a corrected wavefront 440. For example, the wavefront correction apparatus 426 may shift the phase of the light 218 reflected from the eye 204 to minimize image degradation resulting from optical aberrations. The wavefront correction apparatus 426 may be an adaptive optics apparatus in some implementations.

In the illustrated implementation, the wavefront correction apparatus 426 includes a beam splitter 428, a wavefront sensor 430, control electronics 432, and a wavefront corrector 434. The beam splitter 428 may include or be formed of a dichroic mirror, a notch filter, a hot mirror, a cold mirror, and/or other suitable optical elements. Light associated with the aberrated wave front 424 is split such that a portion of the light is directed in the direction 436 and a portion is directed in the direction 438. The portion of light directed in the direction 436 is received at the wavefront sensor 430. The wavefront sensor 430 may be any suitable device for detecting optical aberrations. Some examples include, for example, a Shack-Hartmann wavefront sensor, a Talbot-Moire wavefront sensor, a Tscherning aberrometer, a laser ray tracing aberrometer, or other aberrometry device(s). The wavefront sensor 430 may be in communication with control electronics 432. The beam splitter 428 is configured to direct the portion of light 218 from the optical path in the direction 436 to the control electronics 432 for processing. For example, an electrical signal representative of the deformations in the aberrated wavefront 424, detected by the wavefront sensor 430, may be received at the control electronics 432. The control electronics 432 process the light or signal representative of the light to determine the modifications that should be made by the wavefront corrector 434 to present the corrected wavefront 440. In some implementations, the wavefront corrector 434 is a transmissive element. For example, the wavefront corrector 434 may include or be formed of a translucent (liquid crystal display or LCD) microdisplay, liquid lens, or other suitable adaptive optics component(s). In some examples, the wavefront corrector 434 includes a spatial light modulator available from HOLOEYE Photonics AG of Berlin-Adlershof, Germany. The control electronics 432 may generate and transmit a control signal to the wavefront corrector 434 to modify the phase of incident light (e.g., the light guided in the direction 438) to compensate for the aberrations detected by the wavefront sensor 430. For example, the wavefront corrector 434 is configured to modify a phase of a portion of light 218 directed in the direction 438 based on the processed portion of light directed in the direction 436. The light associated with the corrected wavefront 440 passes through the image shifting apparatus 322 and is received by the surgical microscope 202 such that the user views a higher resolution fundus image. In the implementation of FIG. 4, the wavefront correction apparatus 426 is positioned in the optical path between the indirect non-contact lens 212 and the surgical microscope 202. In other implementations, the wavefront correction apparatus 426 may be positioned anywhere along the optical path between the eye 204 and the surgical microscope 202. For example, the wavefront correction apparatus 426 may be disposed between the prismatic off-axis lens 210 and the indirect non-contact lens 212 or at other locations.

As described above with respect to FIGS. 3A and 3B, the user may rotate the prismatic off-axis lens 210 to view different portions of the periphery of the fundus. The wavefront correction apparatus 426 and/or individual components thereof (e.g., the beam splitter 428, the wavefront corrector 434, etc.) may be sized and shaped to act on the light 218 with the prismatic off-axis lens 210 disposed in any orientation. For example, the beam splitter 426 may be sized and shaped to direct portions of the light 218 in the directions of arrows 436 and 438 when the prismatic off-axis lens 210 is rotated 180° and the illustrated rays representative of the light 218 are positioned above the alignment axis 220 (as shown in FIG. 3B, for example). Similarly, the wavefront corrector 434 may be configured to modify the phase of light 218 illustrated by rays positioned above the alignment axis 220.

In some circumstances, intentional or unintentional movement of the surgical microscope 202, the prismatic off-axis lens 210, the indirect non-contact lens 212, and/or other optical elements may cause a lens surface to touch the cornea 216. Contact between the lens surface and the corneal surface causes a mark that diffuses light 218 and degrades the fundus image. The surgical microscope 202, the prismatic off-axis lens 210, the indirect non-contact lens 212, and/or other optical elements may also inadvertently contact one another. Such contact may damage the optical elements, as well as degrade the fundus image. To prevent contact with the cornea 216 and/or contact between optical elements, the ophthalmic visualization system 400 includes a proximity sensor 442. In the implementation of FIG. 4, the proximity sensor 442 is coupled to the prismatic off-axis lens 210. In other implementations, the proximity sensor 442 may be coupled to a direct contact lens, such as direct contact lens 208, the indirect non-contact lens 212, the surgical microscope 202, and/or other optical elements or structure. The proximity sensor 442 may measure and monitor the distance to the cornea 216 and/or another optical element, and transmit a warning when the distance is less than a threshold value. In some instances, the warning may be a visible warning, an audible warning, a tactile warning, or any combination thereof. In some examples, the threshold value may be selected to be a distance between 3 mm and 40 mm. Other values both larger and smaller are also contemplated. Distances less than the threshold value may indicate a high likelihood of contact.

Figure 5:
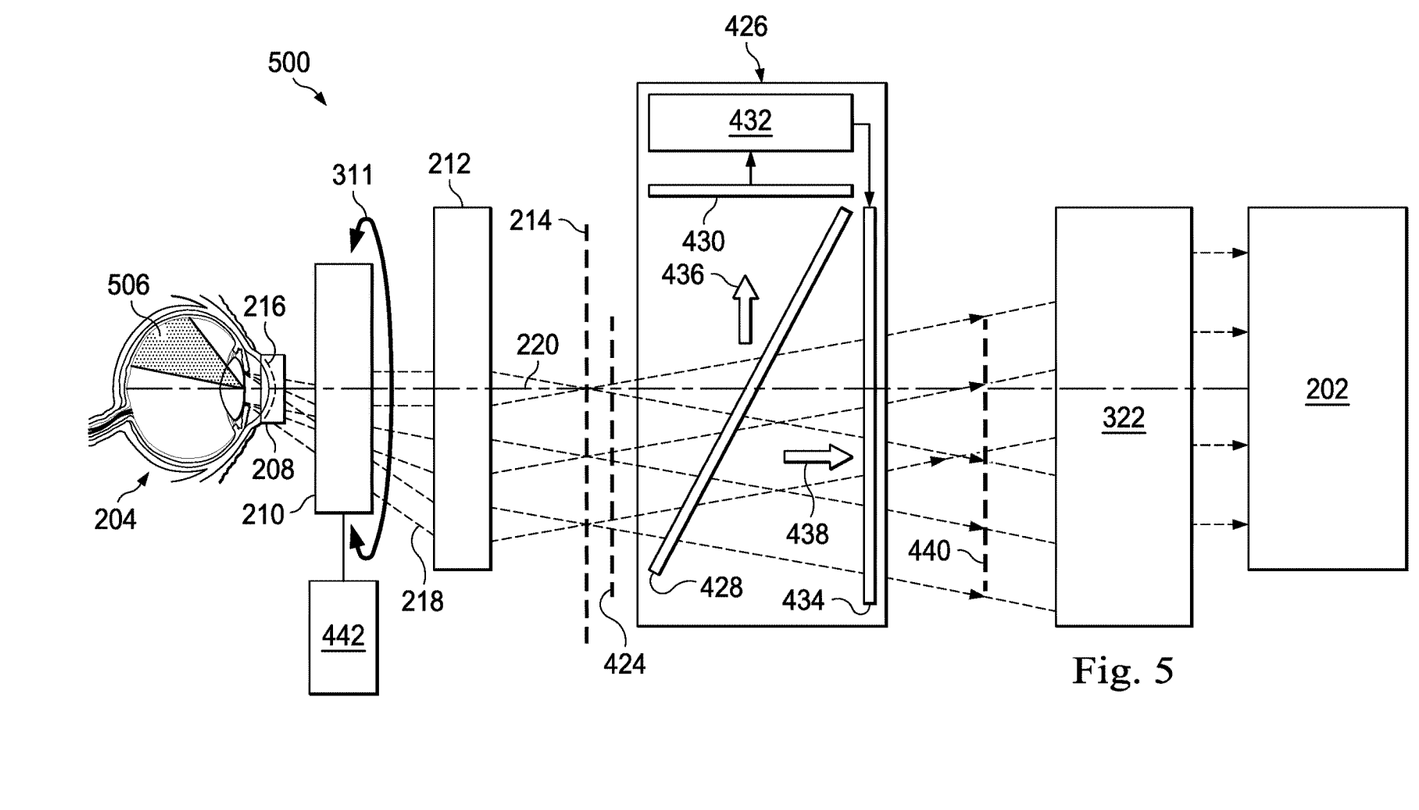
FIG. 5 is an illustration of an example ophthalmic visualization system including a direct contact lens, an indirect non-contact lens, a prismatic off-axis lens, and a wavefront correction apparatus positioned in the optical path.

FIG. 5 illustrates an example ophthalmic visualization system 500. FIG. 5 includes various components that are similar to those described with respect to FIGS. 2, 3, and/or 4. For ease of reading, description of the surgical microscope 202, the eye 204, the direct contact lens 208, the prismatic off-axis lens 210, the indirect non-contact lens 212, the intermediate image plane 214, the imaging shifting apparatus 322, and the wavefront correction apparatus 426 are not repeated here, as these are described with reference to other Figures or implementations herein.

The wavefront correction apparatus 426 is implemented in combination with the direct contact lens 208 in the ophthalmic visualization system 500. As described above with respect to FIG. 3, the direct contact lens 208 minimizes optical aberrations associated with irregularities of the cornea 216. When used in combination with the direct contact lens 208, the wavefront correction apparatus 426 may correct other optical aberrations, such as higher order aberrations. As a result, the ophthalmic visualization system 500 provides the user a relatively higher resolution image of the peripheral field of view 506.

Figure 8:
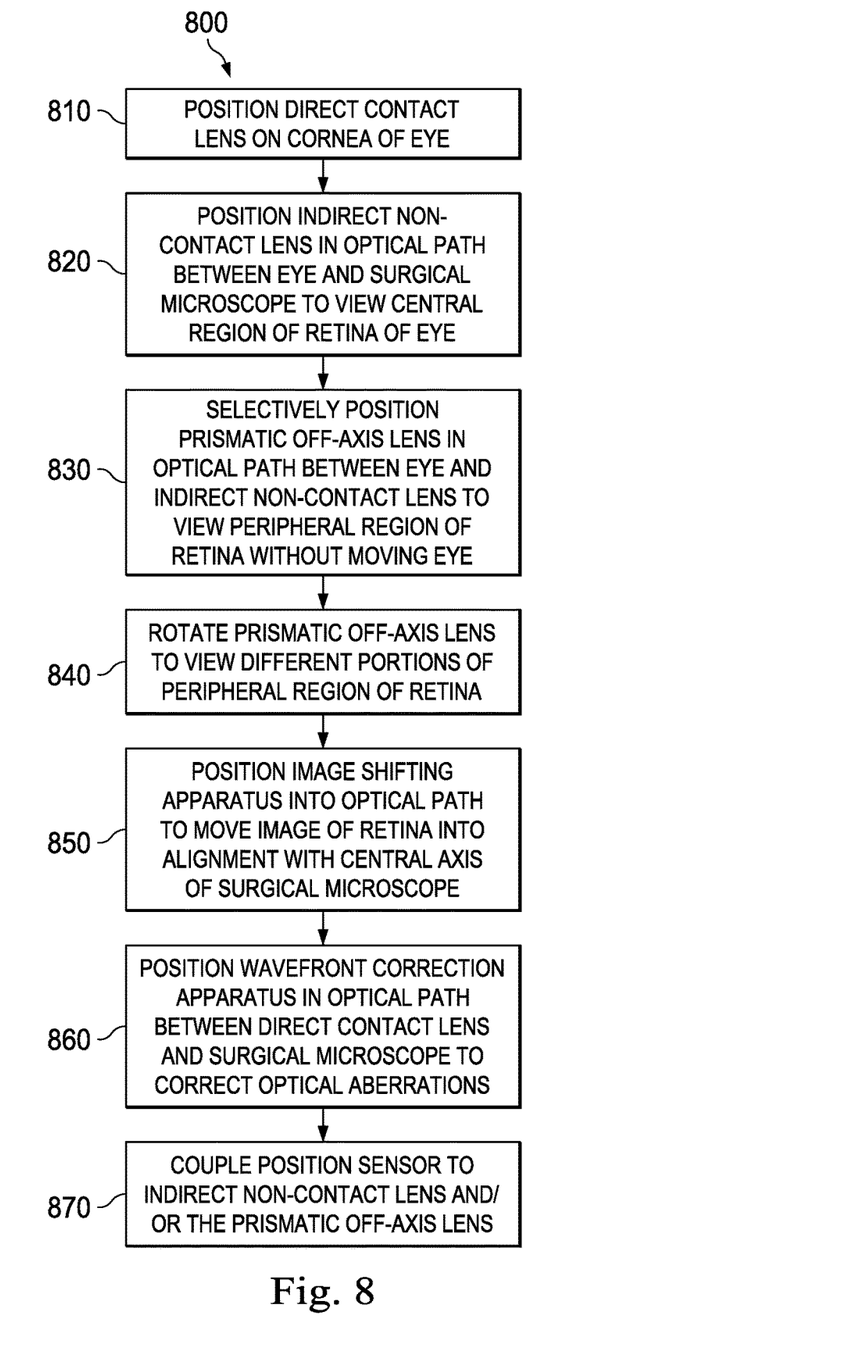
FIG. 8 is an example flowchart illustrating a method of visualizing an eye in an ophthalmic surgical procedure.

FIG. 8 illustrates a flowchart of an example method 800 of visualizing an eye in an ophthalmic surgical procedure. As illustrated, the method 800 includes a number of enumerated steps, but implementations of the method 800 may include additional steps before, after, and in between the enumerated steps. In some implementations, one or more of the enumerated steps may be omitted or performed in a different order.

At step 810, the method 800 includes positioning a direct contact lens on a cornea of an eye. For example, a user, such as a surgeon or other medical professional, may place refractive index-matching gel or fluid on a surface of the direct contact lens. The user may then contact that surface of the direct contact lens to cornea of the eye. Placing the direct contact lens on the cornea may correct aberrations of light reflected from the fundus and transmitted through the eye. In some implementations, the step 810 may be omitted, and as described herein, an indirect non-contact lens and a prismatic off-axis lens may be used view the fundus image. Optical aberrations in such implementations may be corrected by a wavefront correction apparatus, as also described herein.

At step 820, the method 800 includes positioning an indirect non-contact lens in an optical path between the eye and a surgical microscope. For example, the user or the user's assistant(s) may move the patient so that the patient's eye is in alignment with an alignment axis of the surgical microscope, such as when a patient is positioned on a bed below the surgical microscope, or alternatively, may move the surgical microscope to align with the patient. The indirect non-contact lens may be coupled, such as mechanically coupled, to the surgical microscope. Positioning the indirect non-contact lens may include translating, rotating, pivoting, or otherwise moving the indirect non-contact lens. With the direct contact lens and the indirect non-contact lens positioned in the optical path, the user may view the central region of the retina of eye using the surgical microscope. The user may view an image of the fundus and/or retina along an intermediate image plane generated by the indirect non-contact lens.

In some instances, the image generated along the intermediate image plane may be inverted. In such implementations, the method 800 may include steps to invert the fundus image such that the user views an upright image while viewing the eye through the surgical microscope. For example, the method 800 may include positioning an inverter lens in the optical path between the eye and the surgical microscope, such as between the indirect non-contact lens and the surgical microscope. In some implementations, the inverter lens may be part of the optical train of the surgical microscope. In other implementations, the inverter lens may be selectively and/or independently positionable relative to the surgical microscope.

At step 830, the method 800 includes selectively positioning a prismatic off-axis lens in the optical path between the eye and the indirect non-contact lens. The prismatic off-axis lens may be mechanically coupled to the surgical microscope. Positioning the prismatic off-axis lens may include translating, rotating, pivoting, or otherwise moving the prismatic off-axis lens. For example, the user may selectively slide the prismatic off-axis lens into and out of the optical path. With the prismatic off-axis lens positioned in the optical path, the user may view peripheral regions of the retina of eye using the surgical microscope. In that regard, the user may view the peripheral regions of the retina without rotating the eye, indenting the sclera of the eye, and/or otherwise moving eye. The user may also view the peripheral regions without moving the indirect non-contact lens. The method 800 may also include removing the prismatic off-axis lens from the optical path in order to view the central region of the retina.

At step 840, the method 800 includes rotating the prismatic off-axis lens to view different portions of the peripheral region of the retina. The prismatic off-axis lens may be rotatable about an alignment axis of the surgical microscope. For example, the prismatic off-axis lens may be coupled, such as mechanically coupled, to the surgical microscope and/or the indirect non-contact lens such that the prismatic off-axis lens is rotatable about the alignment axis of the surgical microscope. The user may view different portions of the peripheral region of the retina by rotating the prismatic off-axis lens, while the direct contact lens and the indirect non-contact lens remain stationary or otherwise in place.

At step 850, the method 800 includes positioning an image shifting apparatus into the optical path to move the image of retina into alignment with the alignment axis of surgical microscope. Positioning the prismatic off-axis lens in the optical path (step 830) may laterally shift the retina image out of alignment with the surgical microscope. The image shifting apparatus laterally shifts the retina image back into alignment with the surgical microscope such that the user may effectively view the retina image through the surgical microscope.

At step 860, the method 800 includes positioning a wavefront correction apparatus in the optical path, such as, for example, between direct contact lens and the surgical microscope. The wavefront correction apparatus may be configured to correct aberrations in the wavefront of light reflected from the eye. As a result, a higher resolution retina image is generated and viewed by the user.

At step 870, the method 800 includes coupling a proximity sensor to the indirect non-contact lens and/or the prismatic off-axis lens. In some implementations, the proximity sensor may also be coupled to the direct contact lens, the surgical microscope, and/or other optical elements. The method 800 may further include measuring and/or monitoring a distance between the optical elements, and between the eye and the optical element(s). The method 800 may also include providing an alert, such as a visual alert, an auditory alert, a tactile alert, or a combination thereof, when the distance is less than a threshold value, which may be indicative of imminent contact.

The method 800 may further include performing the surgical procedure while visualizing the interior of the eye using the surgical microscope. The surgical procedure may be a posterior segment surgical procedure, such as a pars plana vitrectomy, and/or other desired procedure.

As explained above, the example method described herein may include some of the steps while omitting others. Thus, in some instances, positioning a direct contact lens on a cornea of an eye may be omitted. Thus, while references to the direct contact lens are made in the discussion of the example method 800, it is understood that, in some implementations, the direct contact lens may be included, while, in others, the direct contact lens may be excluded.

Persons of ordinary skill in the art will appreciate that the implementations encompassed by the present disclosure are not limited to the particular exemplary implementations described above. In that regard, although illustrative implementations have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ophthalmic visualization system, comprising:
a first lens positioned relative to a surgical microscope in a manner facilitating viewing of a central region of a retina through the surgical microscope during a surgical procedure, the first lens being positionable in an optical path between an eye and the surgical microscope during the surgical procedure; and
a second lens selectively positionable relative to the surgical microscope and the first lens in a manner facilitating viewing of a peripheral region of the retina of the eye during the surgical procedure, the second lens selectively positionable in the optical path such that the peripheral region is selectively viewable without changing the position of the first lens during the surgical procedure.

2. The system of claim 1, wherein the first lens is an indirect non-contact lens.

3. The system of claim 2, wherein the second lens is a prismatic off-axis lens.

4. The system of claim 3, wherein the second lens is aligned with and rotatable about an alignment axis of the surgical microscope such that different portions of the peripheral region are selectively viewable.

5. The system of claim 1, wherein the first lens is coupled to the surgical microscope.

6. The system of claim 1, wherein the second lens is moveably coupled to the first lens.

7. The system of claim 1, further comprising a third lens positioned and arranged to correct aberrations of light reflected from the eye, the third lens positioned in the optical path adjacent to the eye.

8. The system of claim 7, wherein the third lens is a direct contact lens.

9. The system of claim 1, further comprising a wavefront correction apparatus disposed between the microscope and the first lens, the wavefront correction apparatus being arranged to remove optical aberrations from an image viewable through the microscope.

10. The system of claim 9, wherein the wavefront correction apparatus comprises a beam splitter in the optical path and a wavefront corrector, the beam splitter configured to direct a first portion of light from the optical path for processing, the wavefront corrector being configured to modify a phase of a second portion of light based on the processed first portion.

11. The system of claim 1, further comprising a proximity sensor coupled to at least one of the first lens and the second lens, the proximity sensor being configured to monitor a distance between said at least one of the first lens and the second lens and the eye.

12. The system of claim 1, further comprising an image shifting apparatus structurally configured to move an image of the retina into alignment with an alignment axis of the surgical microscope for viewing.

13. An ophthalmic visualization system, the system comprising:
a direct contact lens positionable on an eye of a patient and in an optical path of a surgical microscope;
a prismatic off-axis lens selectively positionable in the optical path between the direct contact lens and the surgical microscope; and
an indirect non-contact lens positioned in the optical path between the direct contact lens and the surgical microscope;
wherein a peripheral region of a retina of the eye is viewable without moving the eye when the prismatic off-axis lens is positioned in the optical path and a central region of the retina is viewable without moving the eye when the prismatic off-axis lens is removed from the optical path.

14. The system of claim 13, wherein the prismatic off-axis lens is rotatable about an alignment axis of the surgical microscope such that different portions of the peripheral region are selectively viewable.

15. The system of claim 13, further comprising a wavefront correction apparatus positioned in the optical path between the indirect non-contact lens and the surgical microscope, the wavefront correction apparatus being arranged to remove optical aberrations from an image viewable through the microscope.

16. The system of claim 13, further comprising a proximity sensor coupled to at least one of the indirect non-contact lens or the prismatic off-axis lens, the proximity sensor being configured to monitor a distance between said at least one of the indirect non-contact lens and the prismatic off-axis lens and the eye.

17. The system of claim 13, further comprising an image shifting apparatus structurally configured to move an image of the retina into alignment with an alignment axis of the surgical microscope.

18. A method of visualizing an eye undergoing an ophthalmic surgical procedure, the method comprising:

positioning an indirect non-contact lens in an optical path between an eye and a surgical microscope to view a central region of a retina of the eye; and selectively positioning a prismatic off-axis lens in the optical path between the eye and the indirect non-contact lens to view a peripheral region of the retina without moving the eye and without moving the indirect non-contact lens.

19. The method of claim 18, further comprising:
positioning a direct contact lens on a cornea of the eye.
20. The method of claim 18, further comprising:
rotating the prismatic off-axis lens to view different portions of the peripheral region of the retina.

\* \* \* \* \*